United States Patent
Baker et al.

(10) Patent No.: US 8,100,931 B2
(45) Date of Patent: *Jan. 24, 2012

(54) BARIATRIC DEVICE AND METHOD

(75) Inventors: Randal S. Baker, Ada, MI (US); Paul R. Kemmeter, Ada, MI (US); James A. Foote, Ada, MI (US)

(73) Assignee: BFKW, LLC, Ada, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/915,952

(22) Filed: Oct. 29, 2010

(65) Prior Publication Data

US 2011/0092879 A1    Apr. 21, 2011

Related U.S. Application Data

(63) Continuation of application No. 11/463,192, filed on Aug. 8, 2006, now Pat. No. 7,846,174, which is a continuation-in-part of application No. PCT/US2005/36991, filed on Oct. 13, 2005.

(60) Provisional application No. 60/619,308, filed on Oct. 15, 2004, provisional application No. 60/632,147, filed on Dec. 1, 2004, provisional application No. 60/636,845, filed on Dec. 15, 2004, provisional application No. 60/711,310, filed on Aug. 25, 2005.

(51) Int. Cl.
 *A61M 29/00* (2006.01)
(52) U.S. Cl. ..................................................... 606/191
(58) Field of Classification Search .................. 128/898; 623/1.1, 11.11, 23.64, 23.65; 600/97; 606/213–219, 606/139, 192, 191; 604/104–109, 99.01, 604/500
See application file for complete search history.

(56) References Cited

U.S. PATENT DOCUMENTS

| | | | |
|---|---|---|---|
| 4,403,604 | A | 9/1983 | Wilkinson et al. |
| 4,607,618 | A | 8/1986 | Angelchik |
| 5,234,454 | A | 8/1993 | Bangs |
| 5,306,300 | A | 4/1994 | Berry |

(Continued)

FOREIGN PATENT DOCUMENTS

RU    2045233 C1    10/1995

(Continued)

OTHER PUBLICATIONS

"Obesity: Super-Sized Medical Device Market", Start-Up, Mar. 2003, Technology Strategies (Long Article), pp. 1-10.

(Continued)

*Primary Examiner* — Manuel Mendez
(74) *Attorney, Agent, or Firm* — Gardner, Linn, Burkhart & Flory, LLP

(57) ABSTRACT

A bariatric device and method of causing at least partial satiety includes a body that is adapted to be positioned at i) an abdominal portion of the esophagus and/or ii) a proximal cardiac portion of the stomach. The body has a wall defining a lumen. The wall is configured to generally conform to the shape and size of i) the abdominal portion of the esophagus and/or ii) the proximal cardiac portion of the stomach. A force is exerted with the wall at i) the abdominal portion of the esophagus and/or (ii) the proximal cardiac portion of the stomach thereby influencing a neurohormonal feedback mechanism of the patient to cause at least partial satiety by augmenting fullness caused by food and simulating fullness in the absence of food. The method further includes adjusting the force exerted with the wall.

25 Claims, 16 Drawing Sheets

U.S. PATENT DOCUMENTS

| | | | |
|---|---|---|---|
| 5,662,713 | A | 9/1997 | Andersen et al. |
| 5,820,584 | A | 10/1998 | Crabb |
| 6,432,040 | B1 | 8/2002 | Meah |
| 6,558,400 | B2 | 5/2003 | Deem et al. |
| 6,572,627 | B2 | 6/2003 | Gabbay |
| 6,656,194 | B1 | 12/2003 | Gannoe et al. |
| 6,675,809 | B2 | 1/2004 | Stack et al. |
| 6,740,121 | B2 | 5/2004 | Geitz |
| 6,746,460 | B2 | 6/2004 | Gannoe et al. |
| 6,755,869 | B2 | 6/2004 | Geitz |
| 6,773,440 | B2 | 8/2004 | Gannoe et al. |
| 6,802,868 | B2 | 10/2004 | Silverman et al. |
| 6,845,776 | B2 | 1/2005 | Stack et al. |
| 6,960,233 | B1 | 11/2005 | Berg et al. |
| 6,981,978 | B2 | 1/2006 | Gannoe |
| 6,994,095 | B2 | 2/2006 | Burnett |
| 6,994,715 | B2 | 2/2006 | Gannoe et al. |
| 7,025,791 | B2 | 4/2006 | Levine et al. |
| 7,033,373 | B2 | 4/2006 | de la Torre et al. |
| 7,033,384 | B2 | 4/2006 | Gannoe et al. |
| 7,037,344 | B2 | 5/2006 | Kagan et al. |
| 7,044,979 | B2 | 5/2006 | Silverman et al. |
| 7,066,945 | B2 | 6/2006 | Hashiba et al. |
| 7,083,629 | B2 | 8/2006 | Weller et al. |
| 7,087,088 | B2 | 8/2006 | Berg et al. |
| 7,097,650 | B2 | 8/2006 | Weller et al. |
| 7,097,665 | B2 | 8/2006 | Stack et al. |
| 7,146,984 | B2 | 12/2006 | Stack et al. |
| 7,152,607 | B2 | 12/2006 | Stack et al. |
| 7,220,284 | B2 | 5/2007 | Kagan et al. |
| 7,431,725 | B2 | 10/2008 | Stack et al. |
| 7,445,010 | B2 | 11/2008 | Kugler et al. |
| 7,708,752 | B2 | 5/2010 | Durgin |
| 7,846,174 | B2 * | 12/2010 | Baker et al. ............ 606/191 |
| 8,029,455 | B2 | 10/2011 | Stack et al. |
| 2002/0091395 | A1 | 7/2002 | Gabbay |
| 2004/0117031 | A1 | 6/2004 | Stack et al. |
| 2004/0143342 | A1 | 7/2004 | Stack et al. |
| 2004/0220682 | A1 | 11/2004 | Levine et al. |
| 2005/0197715 | A1 | 9/2005 | Kugler et al. |
| 2005/0228504 | A1 | 10/2005 | Demarais |
| 2005/0245957 | A1 | 11/2005 | Starkebaum et al. |
| 2005/0247320 | A1 | 11/2005 | Stack et al. |
| 2005/0283235 | A1 | 12/2005 | Kugler et al. |
| 2006/0020277 | A1 | 1/2006 | Gostout et al. |
| 2006/0074473 | A1 | 4/2006 | Gertner |
| 2006/0089571 | A1 | 4/2006 | Gertner |
| 2006/0155375 | A1 | 7/2006 | Kagan et al. |
| 2006/0190019 | A1 | 8/2006 | Gannoe et al. |
| 2007/0010866 | A1 | 1/2007 | Dann et al. |
| 2007/0166396 | A1 | 7/2007 | Badylak et al. |
| 2007/0276432 | A1 | 11/2007 | Stack et al. |
| 2008/0015523 | A1 | 1/2008 | Baker |
| 2008/0065136 | A1 | 3/2008 | Young |
| 2008/0312678 | A1 | 12/2008 | Pasricha |
| 2009/0177215 | A1 | 7/2009 | Stack et al. |

FOREIGN PATENT DOCUMENTS

| | | |
|---|---|---|
| RU | 94026119 A1 | 8/1996 |
| WO | 2004064685 A1 | 8/2004 |
| WO | 2005037152 A1 | 4/2005 |

OTHER PUBLICATIONS

Andrew S. Lowe, M.D. and Maria B. Sheridan, M.D., "Esphogeal Stenting", Seminars in Interventional Radiology, vol. 21, No. 3, 2004, pp. 157-166.

"Polyflex® Espohageal Stent", Silicone Covered Stent, Boston Scientific, pp. 1-2 and p. 1 of 2, (2004).

Andrew F.R. Dixon, John B. Dixon, and Paul E. O'Brien, "Laparoscopic Adjustable Gastric Banding Induces Prolonged Satiety: A Randomized Blind Crossover Study", The Journal of Clinical Endocrinology & Metabolism, pp. 813-819, 2005.

Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].

Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].

Information pertaining to inventorship of the various claims and lack of obligation to assign, (Jan. 5, 2010).

International Search Report and Written Opinion of the International Searching Authority from corresponding Patent Cooperation Treaty (PCT) Application No. PCT/US05/36991, mailed Mar. 31, 2006.

Summary of Official Action dated Oct. 29, 2009, from the Israel Patent Office in a patent application corresponding to the present application.

Lowe, Andrew S., M.D. and Sheridan, Maria B., M.D., "Esophageal Stenting," annotated by Israel Patent Office, (2004).

Abstract and claims of U.S. Patent 6,960,233 annotated by the Israel Patent Office, (Nov. 1, 2005).

* cited by examiner

BARIATRIC DEVICE AND METHOD

CROSS REFERENCE TO RELATED APPLICATIONS

The present invention is a continuation of U.S. patent application Ser. No. 11/463,192, filed on Aug. 8, 2006, which is continuation-in-part application of International Application No. PCT/2005/036991, filed on Oct. 13, 2005, entitled BARIATRIC DEVICE AND METHOD, which claims the benefit of 60/619,308 filed on Oct. 15, 2004; and claims the benefit of 60/632,147 filed on Dec. 1, 2004; and claims the benefit of 60/636,845 filed on Dec. 15, 2004; and claims the benefit of 60/711,310 filed on Aug. 25, 2005, the disclosures of which are incorporated herein in their entirety.

BACKGROUND OF THE INVENTION

The present invention is directed to a bariatric device and method of causing at least partial satiety in a patient. In particular, the present invention is directed to a bariatric device and a method of causing at least partial satiety in a patient by a noninvasive or minimally invasive technique.

Obesity is a large and increasing problem in the United States and worldwide. In round numbers, from the period encompassing the year 1990 to the period encompassing the year 2000, the prevalence of overweight people (BMI greater than 25) increased from 56 percent of United States adults to 65 percent and the prevalence of obese adults (BMI greater than 30) increased from 23 percent to 30 percent. Likewise, the prevalence of overweight children and adolescents (ages 6-19 years) increased from 11 percent in the period encompassing the year 1990 to 16 percent in the period encompassing the year 2000. The increasing prevalence of overweight among children and adolescents will make the problem even greater when they reach adulthood. The problem is not limited to the United States. Between 10 percent and 20 percent of European men are obese and between 10 percent and 25 percent of European women are obese. Numerous medical conditions are made worse by obesity including Type II diabetes, stroke, gallbladder disease and various forms of cancer. Approximately 500,000 people in North America and Western Europe are estimated to die from obesity-related diseases every year and obesity is estimated to affect more than one billion adults worldwide. Therefore, there is a pressing and unmet need for a solution to the epidemic problem.

Various techniques are known for reducing obesity in patients. Known techniques tend to be based upon restricting food movement and/or nutrient absorption. One example is gastric bypass surgery on the patient, which is highly invasive. The goal of such surgery is to form a pouch from a portion of the stomach to reduce the volume of the space in the stomach receiving food. When the patient ingests food, the pouch is filled which stretches the stomach wall and produces satiety. One difficulty with such procedure is that it requires food to fill the pouch to create satiety. As a result, dietary restrictions are required for effective operation of the pouch. Such restrictions include withholding of liquids during meals to avoid washing the food from the pouch. Also, liquids with substantial calories tend to pass through the pouch without creating substantial satiety. Moreover, the opening from the pouch tends to become enlarged over time, thus allowing more food to pass while achieving reduced satiety. Thus, patients undergoing such surgical techniques often experience gradual weight gain over time.

Alternative weight loss devices and methods have been proposed. However, such devices and methods may be difficult to place in the patient, have questionable efficacy, and may cause undesirable side effects.

SUMMARY OF THE INVENTION

The present invention utilizes a new principle of implied satiation. The present invention provides a bariatric device and method of causing satiety in a patient that augments the natural response of the body. This may be accomplished using a non-invasive or minimally invasive procedure with a device that may be removable or absorbable. Moreover, satiety may be caused in a manner that does not interfere with other body functions, such as operation of normal reflux mechanism, bile ducts, taking of medications, and the like. The implied satiation technique of the present invention does not rely on either the restrictive or malabsorptive techniques of the prior art.

A bariatric device, according to an aspect of the invention, includes a body having a wall defining a lumen. The wall is configured to generally conform to the shape and size of i) the abdominal portion of the esophagus and/or ii) the proximal cardiac portion of the stomach. The wall is adapted to exert a force on i) the abdominal portion of the esophagus and/or ii) the proximal cardiac portion of the stomach thereby influencing a neurohormonal feedback mechanism to cause at least partial satiety by augmenting fullness caused by food and simulating fullness in the absence of food. The body is adapted to adjust the force exerted by the wall.

The force may be adjustable endoscopically. The wall may define a chamber wherein adjustment of an amount of fluid in the chamber adjusts the force exerted by the wall. A port may provide external access to the chamber.

A control may be provided to adjust the force exerted by the wall. The control may temporally adjust the force exerted by the wall. The control may be programmed to adjust the force exerted by the wall based upon the time of day. The control may be programmed to increase the force exerted by the wall during anticipated waking hours and to decrease the force exerted by the wall during anticipated sleeping hours. The control may be programmed to increase the force exerted by the wall at anticipated eating times. The control may be adapted to adjust the force exerted by the wall based upon hormonal levels. Another control may be provided that is an external control with a radio-frequency link between the control and the external control.

The body may include tissue in-growth characteristics. The body may be made at least in part from an absorbable material. The lumen may be substantially free of restriction. The wall may be adapted to exert a force without the presence of food.

A bariatric device, according to another aspect of the invention, includes a body having a wall defining a lumen. The wall includes a wall portion defining an esophageal member sized to conform to an abdominal portion of the esophagus, another wall portion defining a cardiac member sized to conform to a proximal cardiac portion of the stomach and a further wall portion extending between the esophageal member and the cardiac member. The esophageal member and the cardiac member are adapted to exert a force on the abdominal portion of the esophagus and the proximal cardiac portion of the stomach thereby influencing a neurohormonal feedback mechanism to cause at least partial satiety by augmenting fullness caused by food and simulating fullness in the absence of food. The body is adapted to adjust the force exerted by the esophageal member and the cardiac member.

A bariatric device, according to yet another aspect of the invention, includes a body having a wall defining a lumen. The wall is configured to generally conform to the shape and size of i) the abdominal portion of the esophagus and/or ii) the proximal cardiac portion of the stomach. The wall is adapted to exert a force on i) the abdominal portion of the esophagus and/or ii) the proximal cardiac portion of the stomach thereby influencing a neurohormonal feedback mechanism to cause at least partial satiety by augmenting fullness caused by food and simulating fullness in the absence of food. A mechanism is incorporated into the body. The mechanism is adapted to increase or decrease the force exerted on i) the abdominal portion of the esophagus and/or ii) the proximal cardiac portion of the stomach.

A method of causing at least partial satiety, according to an aspect of the invention, includes positioning a body at i) an abdominal portion of the esophagus and/or ii) a proximal cardiac portion of the stomach. The body has a wall defining a lumen. The wall is configured to generally conform to the shape and size of i) the abdominal portion of the esophagus and/or ii) the proximal cardiac portion of the stomach. A force is exerted with the wall at i) the abdominal portion of the esophagus and/or (ii) the proximal cardiac portion of the stomach thereby influencing a neurohormonal feedback mechanism of the patient to cause at least partial satiety by augmenting fullness caused by food and simulating fullness in the absence of food. The method further includes adjusting the force exerted with the wall.

The adjusting may include increasing or decreasing the force exerted with the wall. The method may include monitoring a level of satiety. The adjusting the force may include adjusting the force at the time of positioning said body. The adjusting the force may include adjusting the force according to a temporal parameter.

A method of causing at least partial satiety, according to another aspect of the invention, includes positioning a body at the abdominal portion of the esophagus and the proximal cardiac portion of the stomach. The body has a wall defining a lumen. The wall includes a wall portion defining an esophageal member sized to conform to the abdominal portion of the esophagus, another wall portion defining a cardiac member sized to conform to the proximal cardiac portion of the stomach and a further wall portion extending between the esophageal member and the cardiac member. A force is exerted with the esophageal member and the cardiac member on the abdominal portion of the esophagus and the proximal cardiac portion of the stomach thereby influencing a neurohormonal feedback mechanism to cause at least partial satiety by augmenting fullness caused by food and simulating fullness in the absence of food. The method further includes increasing or decreasing the force exerted with the esophageal member and the cardiac member.

A method of causing at least partial satiety, according to yet another aspect of the invention, includes positioning a body at i) an abdominal portion of the esophagus and/or ii) a proximal cardiac portion of the stomach. The body has a wall defining a lumen. The wall is configured to generally conform to the shape and size of i) the abdominal portion of the esophagus and/or ii) the proximal cardiac portion of the stomach. A force is exerted with the wall at i) the abdominal portion of the esophagus and/or (ii) the proximal cardiac portion of the stomach thereby influencing a neurohormonal feedback mechanism of the patient to cause at least partial satiety by augmenting fullness caused by food and simulating fullness in the absence of food. The body further includes a mechanism that is adapted to adjust the force exerted on i) the abdominal portion of the esophagus and/or ii) the proximal cardiac portion of the stomach. The method further includes increasing or decreasing the force using the mechanism.

Thus, it can be seen that embodiments of the present invention provide an implied satietor and implied satiation method that does not require food to generate the satiety through the neurohormonal mechanism of the body. This advantageously produces at least partial satiety in the patient in the absence of food, as well as augmenting fullness caused by food during the ingestion of the food. Moreover, because satiety is not caused by food, the patient would not necessarily need to be subject to dietary restrictions, such as withholding of liquids during meals or withholding of liquids having substantial calories.

Moreover, in contrast to surgical procedures, embodiments of the present invention provide a bariatric device and method of causing at least partial satiety that is minimally invasive and which avoids many of the potential side effects of gastric bypass surgery and other surgical procedures, such as adjustable gastric banding, and the like. Also, because of the placement of the device, there is no interference with operation of gastric functions, such as with the bile ducts, and the like. Further, as previously noted, the bariatric device can be adapted to allow the gastro-esophageal junction to function normally without any significant interference or impediment. Also, embodiments of the invention provide a bariatric device and method of inducing at least partial satiety in the patient that does not operate on the basis of causing flu-like symptoms in the patient in a thwarted effort to attempt to induce the patient to eat less, such as may occur by the placement of devices in the patient's duodenum, or the like.

Additionally, in contrast to pouches formed in gastric bypass surgery, embodiments of the present invention do not include a discharge opening that is subject to enlargement with the passage of time, thereby eliminating at least one source of gradual weight gain in patients undergoing gastric bypass surgery.

Moreover, because it is a non-invasive or minimally invasive procedure, embodiments of the present invention may be applied not only to morbidly obese patients, but to obese patients, overweight patients, adolescents, and potentially even children.

Thus, it is seen that the present invention is embodied in a bariatric device and method including a body having an expandable wall which evokes normal neurohormonal responses associated with fullness or satiety. The body wall does so by acting on one or more portions of the distal esophagus and/or the cardia of the patient. The normal filling sensation of the stomach is augmented and amplified. Further, it has been found that the body appears to have a "satiety continuum" where a person transitions from hungry, which is on one end of the continuum or spectrum where there is a lack of satiety, to lacking hunger or being satisfied after eating and to being full with continued consumption. If the person continues to eat to the point of overeating, the person then becomes nauseous, which represents the other end of the continuum. As the pressure applied to the distal esophagus and/or the cardia of a patient is increased, the further along the patient will be on this "continuum" or spectrum. Ideally, then for an extremely overweight person, the bariatric device of the present invention may be best used if sufficient pressure is applied so that the patient is on the nausea end of the spectrum or just below at a "sub-nausea" point.

These and other objects, advantages and features of this invention will become apparent upon review of the following specification in conjunction with the drawings.

DESCRIPTION OF THE PREFERRED EMBODIMENT

Figure 1:
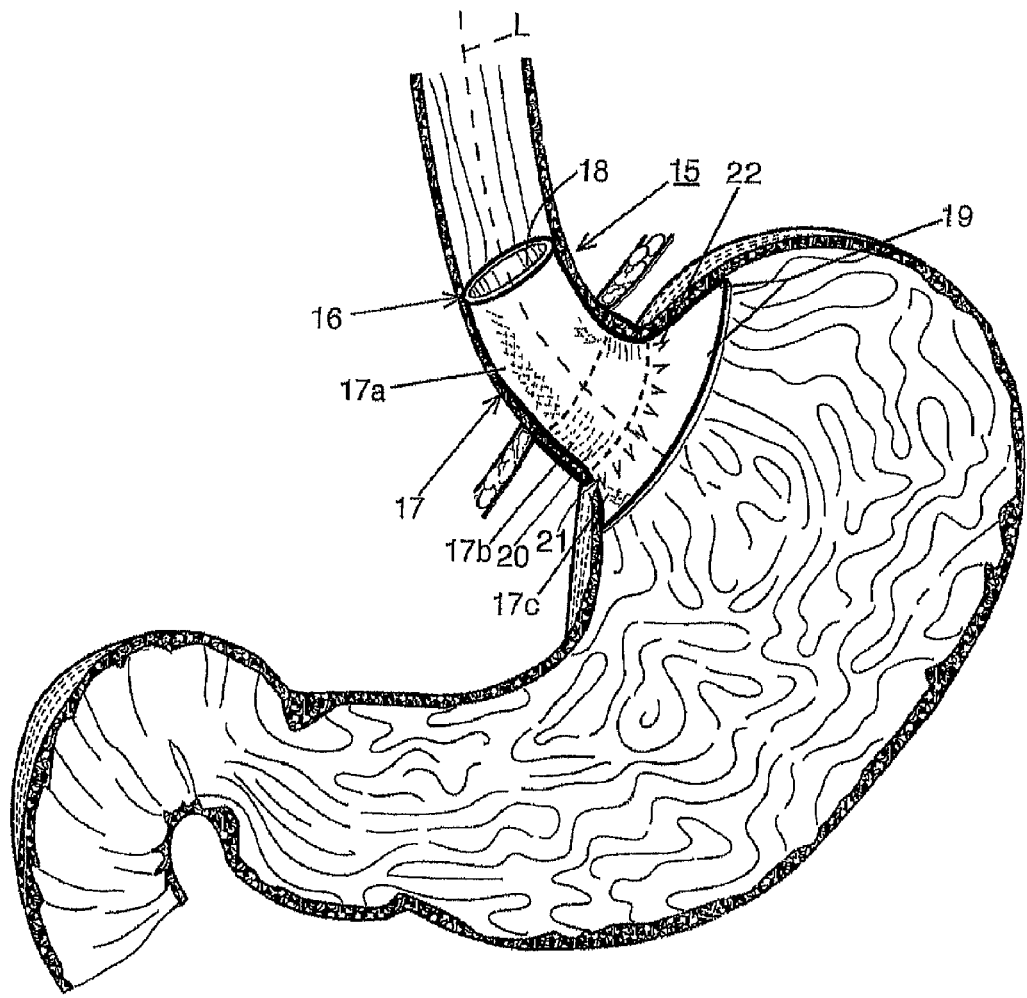
FIG. 1 is a diagram of a bariatric device positioned at the abdominal portion of the esophagus, the esophageal-gastric junction and the proximal cardiac portion of the stomach of the patient.

Referring now specifically to the drawings, and the illustrative embodiments depicted therein, a bariatric device, or implied satietor, 15, which causes satiety by acting on the abdominal portion of the esophagus, and/or the esophageal-gastric junction and/or the proximal cardiac portion of the stomach, is illustrated in FIG. 1 being positioned in the patient. Device 15 includes a body 16 having an expandable wall 17 thereby defining a transverse passage, or lumen 18 through the body. Body 16 is designed to conform to the shape and size of the abdominal portion of the esophagus, the esophageal-gastric junction and/or the proximal cardiac portion, or cardia, of the patient's stomach. The present invention is embodied in various bariatric devices. The devices may be removable, absorbable and/or permanent. The devices may be manufactured from a synthetic or a bioprosthetic material. While the invention is illustrated with a mesh wall, other configurations are possible, such as coil configurations, and the like. Bariatric device 15 may be positioned utilizing various techniques, such as endoscopic placement with fluoroscopic assist.

Wall 17 is configured to exert an outward pressure, typically a generally radial outward pressure, at the abdominal portion of the esophagus, the esophageal-gastric junction and/or the cardia of the patient. This may be accomplished, for example, by configuring the wall to have a proximal portion 17a to create an interference fit with the abdominal portion of the esophagus and/or a central portion 17b configured to create an interference fit with the esophageal-gastric junction and/or a distal portion 17c configured to create an interference fit with the patient's cardia. The pressure exerted by wall portions 17a, 17b and/or 17c influences the neurohormonal feedback mechanism present at the esophagus and/or stomach to cause at least partial satiety. As will be discussed in more detail below, the pressure exerted by the extendable wall may be fixed or adjustable. The force that influences the neurohormonal feedback mechanism present at the abdominal portion of the esophagus, the esophageal-gastric junction and/or the cardiac portion of the stomach is intended to be relatively consistent over as large an area as reasonably possible. The force exerted by the wall of the bariatric device is believed to activate stretch receptors located in the abdominal portion of the esophagus, the esophageal junction and/or the cardia. In contrast to prior proposed devices, which require that the patient ingest food in order to influence neurohormonal feedback mechanisms, bariatric device 15 simulates fullness in the absence of food. It also augments fullness caused by food.

This interference fit may be created by a self-extendable, or self-expanding, wall. Alternatively, it may be created by an extendable wall, such as a balloon-extendable wall. The extended wall diameter is chosen so that it is somewhat oversized compared to the diameter of the conduit in which it is positioned, namely, the abdominal portion of the esophagus, the esophageal-gastric junction and/or the cardia. A self-extendable wall may be, by way of example, formed from a material, such as metal, fibers or fibrous materials, including carbon fibers, and may be a wall made from a self-extendable silicone-coated material. For example, the wall may be formed from a metal sheet, such as a Nitinol sheet, formed for example, by laser cutting, or from a coil or lattice structure formed from a metal or carbon fiber, which may be encapsulated or embedded in an insert polymer, such as silicone or the like. Alternatively, the wall may be extended by a balloon or fluid extendable reservoir expanding the wall outwardly, including generally radially outwardly, to a position firmly against the wall of the conduit in which the body is inserted. This inflation may be accomplished endoscopically with a blunt needle or with a control as will be discussed in more detail below.

As can be seen in FIG. 1, wall 17 is longitudinally non-symmetrical with respect to the central longitudinal axis "L" defined by the direction of movement of the food along the patient's esophagus and stomach. In particular, as one moves along axis L, the cross-sectional configuration of wall 17 varies proximally to distally. For example, wall portions 17a and 17b are generally cylindrical in shape and wall portion 17c is frusto-conical in shape, flaring outwardly from a distal end of wall portion 17b. Wall portion 17c is angled to conform to the cardiac notch. Wall 17 may also be radially non-symmetrical with respect to this longitudinal axis "L". In particular, certain portions of wall 17 are at a greater radial distance from axis L than portions of the wall at a different location around axis L. For example, wall portion 17c is enlarged at 19 to extend to more of the fundus of the cardia, such as the angle of His. This enlarged portion 19 makes wall 17 radially non-symmetrical with respect to axis "L".

The narrow portion of lumen 18, which generally is the portion in the patient's esophagus, may have a length that is no longer required to provide enough force to produce satiety. In the illustrative embodiment, the narrow portion of lumen 18 is less than 9 cm in length. In certain embodiments, the narrow portion of lumen 18 is in the range of between 6 cm and 7 cm in length. This reduces the tendency of food to get caught in the lumen as well as any interference with peristalsis of the esophagus while producing force over a sufficient surface area to produce satiety.

In the embodiment illustrated in FIG. 1, bariatric device 15, and corresponding method of causing satiety in a patient, includes providing at least a portion 20 of middle wall portion 17b that does not exert a substantial pressure or force. Such portion may be made from a flaccid material, such as a non-self-expandable material, or may be formed from a plurality of discrete wall portions that simply connect the proximal portion 17a to the distal portion 17c, as more fully described in reference to FIG. 14A below. These discrete wall portions may be interconnected to form a mesh or may be unconnected from each other to simply act as connectors between the proximal portion 17a and the distal portion 17c. The device would be positioned such that the non-self expanding portion 20 covers the gastro-esophageal sphincter. This would allow the anti-reflux mechanism of the gastro-esophageal junction to operate generally normally because the wall of portion 20 would not exert any significant pressure on the sphincter. This embodiment allows the patient to belch, vomit, and the like, while resisting reflux. In bariatric device 15, proximal wall portion 17a is self-expandable and is generally cylindrical in shape to conform to the shape and size of the abdominal portion of the esophagus and distal wall portion 17c is self-expandable and is generally frusto-conically in shape to conform to the shape and size of the proximal cardiac portion of the stomach.

Bariatric device 15 may include a fixation system 21, which is capable of resisting distal migration of the device. Fixation system 21 may include a series of anchors 22 illustrated as a series of V-shaped downwardly directed appendages from wall 17. Alternatively, the anchors may be in the shape of downwardly directed barbs or hooks, metallic anchors extending radially from said body, or the like. Such arrangement provides fixation against migration, typically distal migration, while allowing the device to be easily removed from the patient because the anchors may be configured to provide less resistance to proximal movement. In the embodiment illustrated in FIG. 1, the anchors are positioned at or near the esophageal-gastric junction, such as proximally at distal portion 17c of the wall. This positioning of the anchor takes advantage of the fact that the esophageal gastric junction is thicker and, therefore, stronger at this location.

Figure 2:
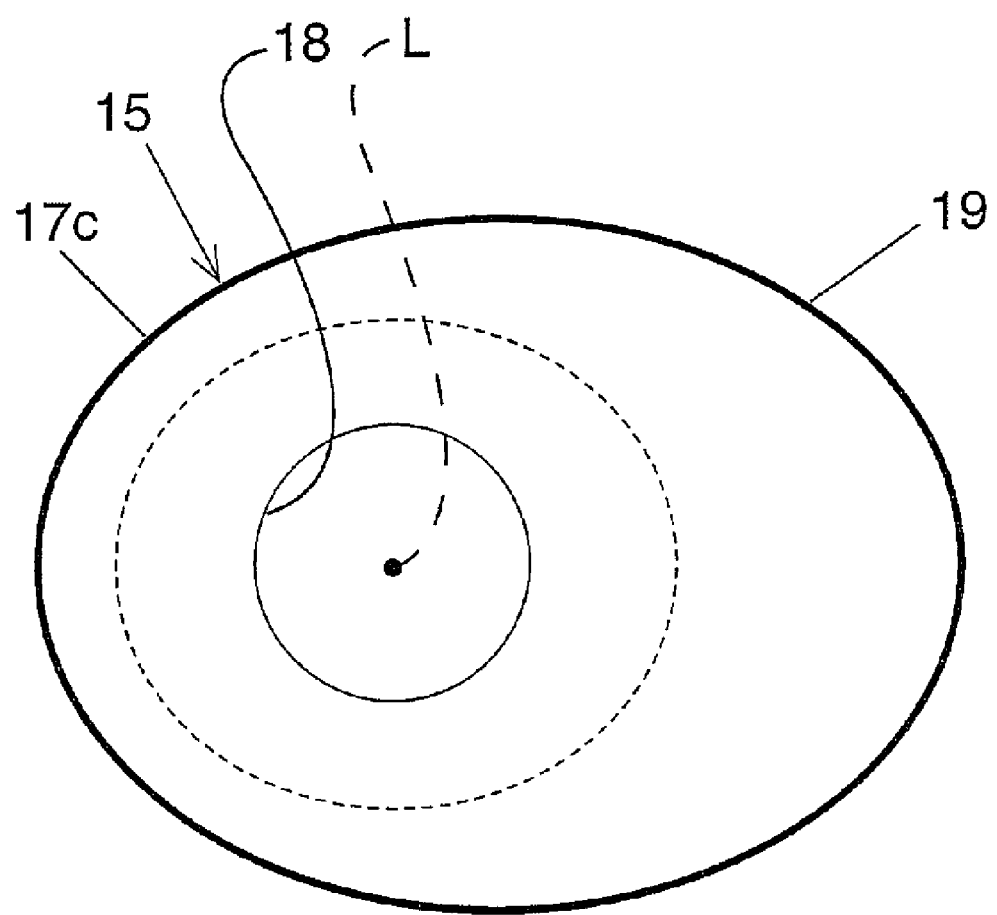
FIG. 2 is a perspective view of an alternative embodiment of the bariatric device in FIG. 1.
Figure 3:
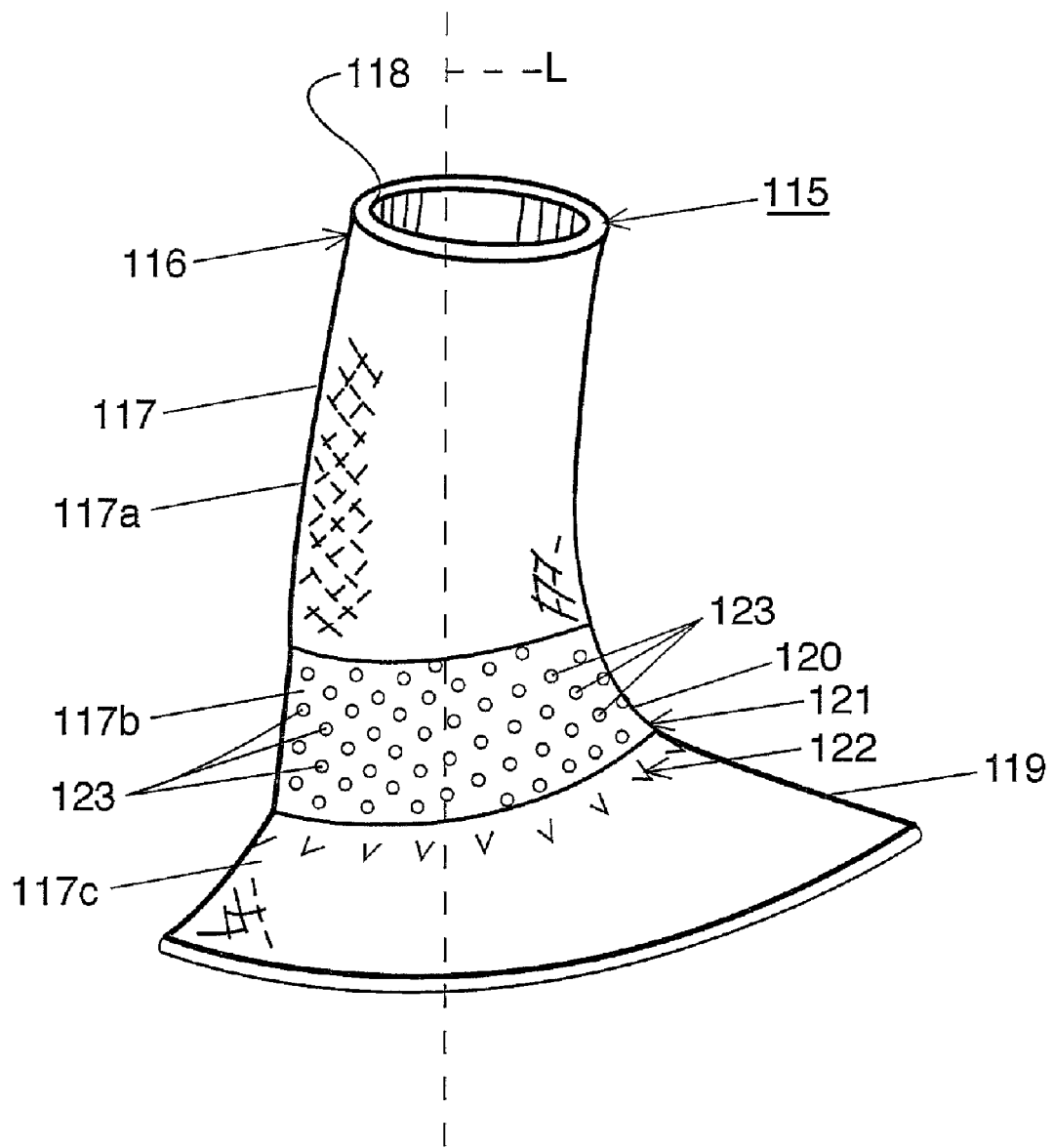
FIG. 3 is a bottom plan view of the bariatric device in FIG. 2.

A bariatric device 115 includes a wall 117 having a proximal wall portion 117a that applies outward pressure, such as generally radially outward pressure, to the abdominal portion of the esophagus, a distal portion 117c that applies outward pressure, such as generally radially outward pressure, to the proximal cardiac portion of the stomach, and a middle portion 117b that is positioned at the esophageal-gastric junction (FIG. 2). As with bariatric device 15, in bariatric device 115 the central portion 117b is made from a non-expandable material, such as a flaccid material 120. Also, distal portion 117c includes an enlarged portion 119 that extends to more of the function of the cardia, such as the angle of His. Flaccid material 120 includes openings 123 that allow ingrowth of material. Openings 123 define at least in part a fixation system 121. Fixation system 121 may include a secondary, or temporary, means for anchoring bariatric device 115 while allowing tissue to ingrowth through openings 123. Such secondary fixation system may include stitches, staples, or the like. Openings 123 may be sized appropriately to accept such stitches or staples. The sutures could be dissolvable or non-dissolvable. Openings 123 may be as few as, for example, five openings in the flaccid material portion 120. Alternatively, they may be a lattice of small holes that allow tissue ingrowth. The use of tissue ingrowth utilizes the body's reaction to the bariatric device 115 in order to assist in fixing the device against distal migration. Further, the tissue ingrowth, which results from the mucosa essentially incorporating the device into the anatomy of the patient, provides resistance to infection. This ingrowth can be in a portion of the device body or through the entire device body. While some irritation of the mucosa may occur when bariatric device 115 is removed, any such irritation should be relatively minor and readily healed. As with all fixation systems described herein, fixation system 121 may be used in combination with other fixation systems, such as fixation system 21, or the like. Alternately, the tissue ingrowth may be used to promote permanence—in other words to incorporate the device into the body of the patient.

Figure 4:
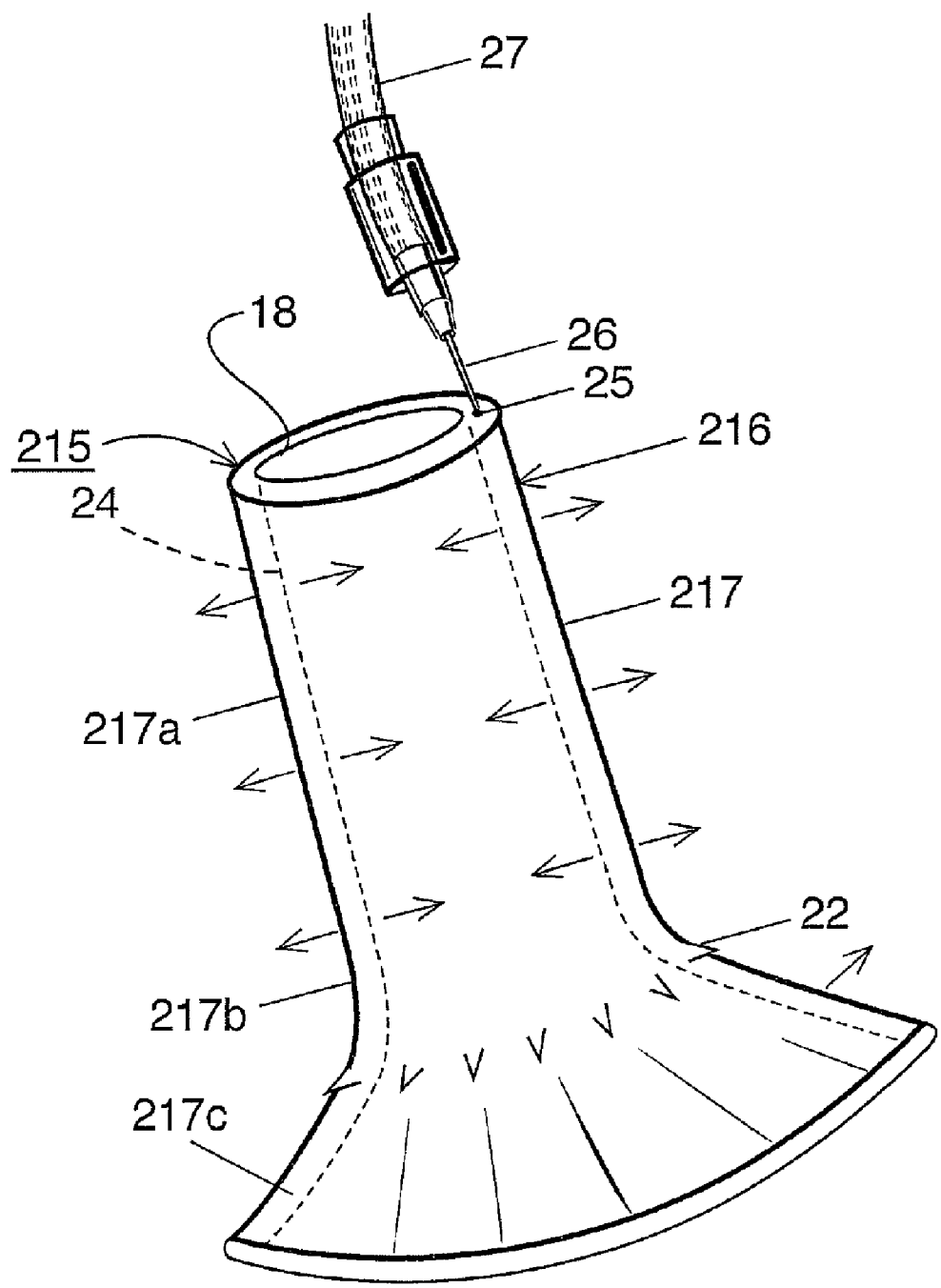
FIG. 4 is the same view as FIG. 2 of another alternative embodiment.
Figure 5:
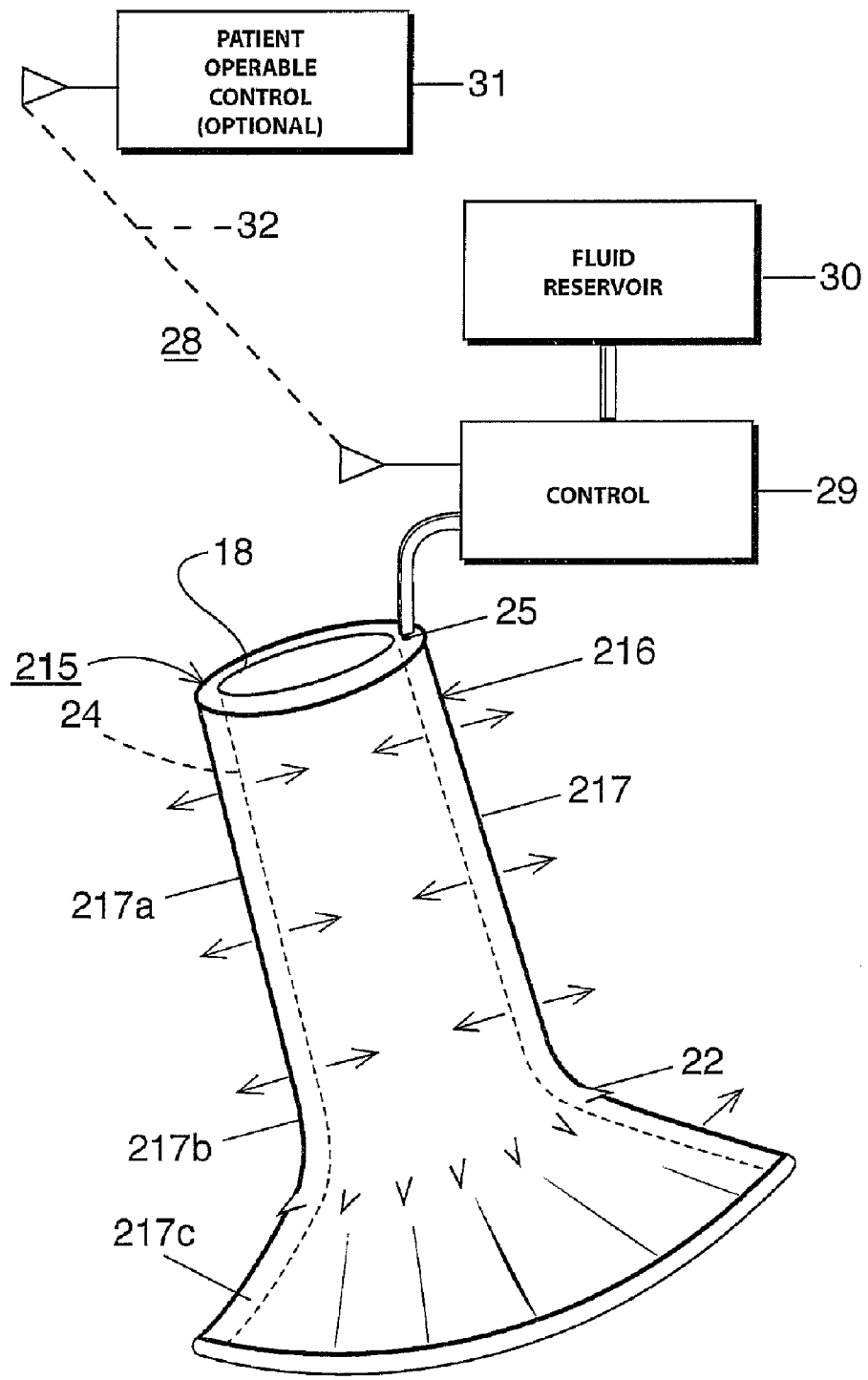
FIG. 5 is the same view as FIG. 4 illustrating an alternative control technique.

An alternative bariatric device 215 includes a body 216 having an expandable wall 217 (FIGS. 4 and 5). Expandable wall 217 defines an internal chamber 24 throughout at least a portion of the proximal portion 217a, middle portion 217b and distal portion 217c of wall 217. Chamber 24 may be a single unitary chamber that extends the length of wall 217 or may be a series of separate chambers that are either interconnected or separated from each other. For example, a chamber may be positioned around proximal portion 217a of wall 217 that is sized and shaped to be positioned at the patient's abdominal esophagus and a chamber may be positioned at distal portion 217c that is sized and shaped to be positioned at the patient's cardia while no chamber is present at all or a portion of 217b that is configured in size to be at the esophageal-gastric junction of the patient. In this manner, wall 217 would not be substantially expandable at the gastro-esophageal sphincter, thereby reducing interference with normal operation of such sphincter, as previously discussed.

As can be seen in FIG. 4, a port 25 may be provided to chamber 24 in order to allow access by a needle 26 connected with a device 27 that is endoscopically inserted in the patient and used to either add fluid to or remove fluid from chamber 24. In this manner, the amount of force exerted by wall 217 may be varied or adjusted. In this manner, for example, a greater amount of force may be applied to a morbidly obese patient, such as one that is more than 40 pounds overweight, while a lower amount of pressure may be applied to patients that are overweight or mildly obese, such as those that are 30 to 40 pounds overweight, for example. Bariatric device 25 is illustrated with a fixation system in the form of anchors 22, although other fixation systems previously described may be utilized. Additionally, distal portion 217c may be radially symmetrical with respect to the longitudinal axis "L" of the device or may be non-symmetrical by including the enlarged portion of distal wall portion 217c as previously described.

As illustrated in FIG. 5, reservoir 24 of bariatric device 215 may, alternatively, be connected with a fluid reservoir 28 positioned within the patient and including a control 29 that is configured to selectively transfer between fluid reservoir 24 in the bariatric device and fluid reservoir 28 in the patient. In this manner, control 29 may control the amount of fluid in fluid chamber 24, thereby adjusting the amount of force exerted by the wall 217 of the device on the conduit in which it is positioned. An optional patient operable control 31 may be provided and interconnected with internal control 29, such as by a radio-frequency link 32, in order to allow a patient or medical attendant to modify the amount of pressure exerted by wall 217.

Control 29 may provide for a temporal adjustment of the amount of pressure exerted by bariatric device 215 on the patient's distal esophagus and/or proximal stomach. By way of example, control 29 may include an algorithm that causes fluid to be transferred from fluid reservoir 30 to fluid chamber 24 of the device 215 in order to increase the amount of pressure, typically radial pressure, exerted by wall 217 during general waking hours of the patient when satiety is desired. Control 29 can further be programmed to transfer fluid from reservoir 24 to reservoir 30 during periods of time when the patient is expected to be sleeping and satiety is not required.

Patient control 31 may, alternatively, allow manual adjustment of the amount of force exerted by wall 214 of device 215. For example, when the patient retires at night, the patient may operate user control 31 in order to instruct control 29 to transfer fluid from chamber 24 to fluid reservoir 30, thereby reducing pressure exerted by wall 217. When the patient awakes, the patient may then utilize user control 31 in order to cause control 29 to increase the amount of pressure exerted by wall 217. This temporal control of the amount of force exerted by wall 217 should overcome any potential tachy phylaxis that may result in the diminishing response of the neurohormonal system of the patient to the force exerted by wall 217. Alternatively, the temporal control may be utilized, where appropriate, to adjust the amount of pressure with respect to eating times of the patient, or the like. Control 29 may, alternatively, monitor certain hormonal levels of the patient in order to determine when the patient is expected to eat a meal and may even be a self-learning control system in order to learn the variations in the patient's hormonal levels.

Figure 6:
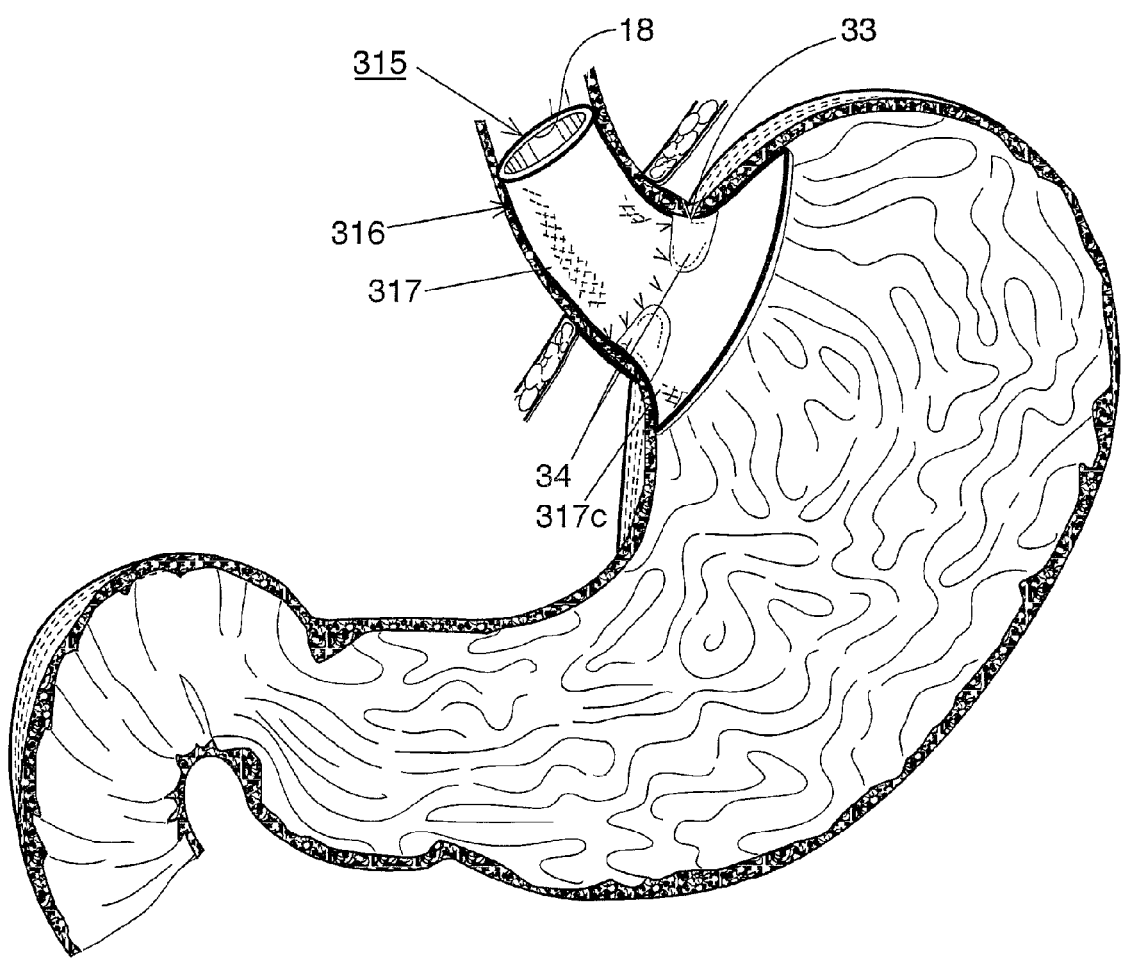
FIG. 6 is the same view as FIG. 2 of yet another alternative embodiment.
Figure 7:
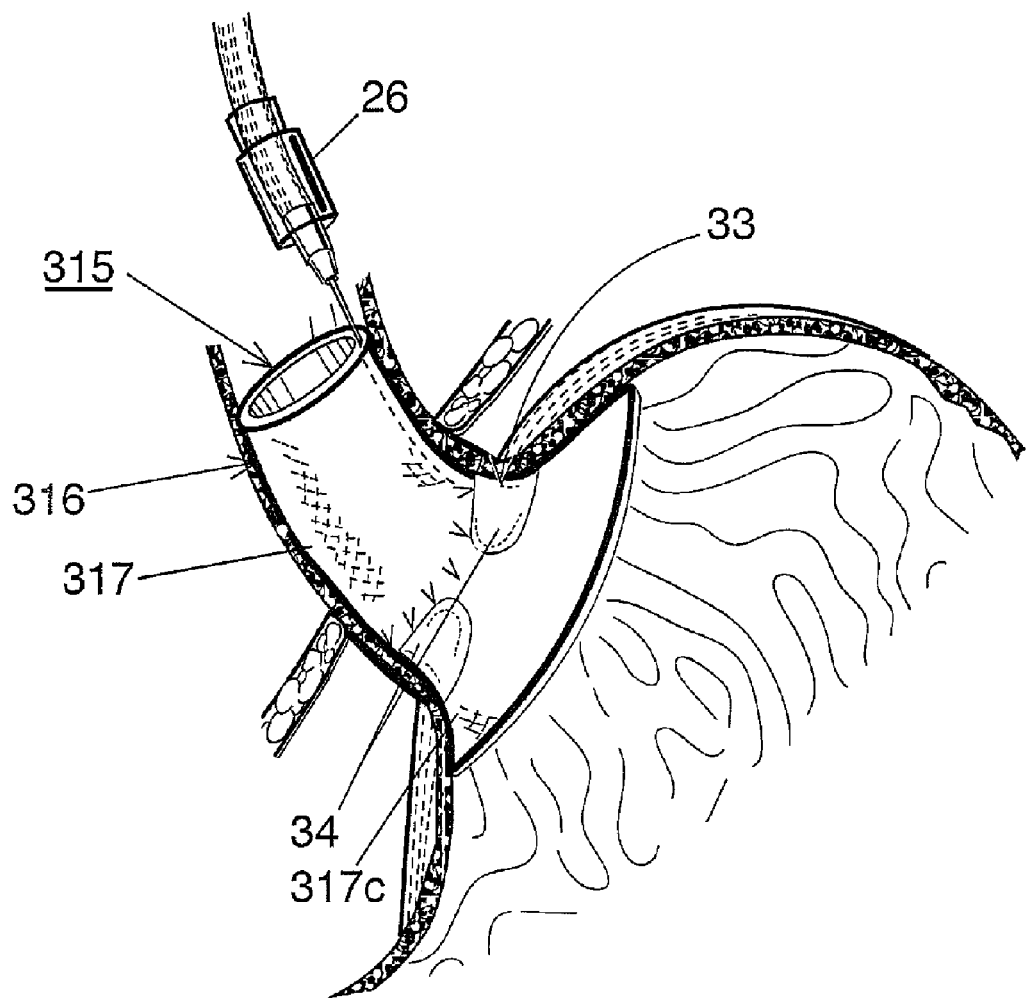
FIG. 7 is the same view as FIG. 6 illustrating adjustment of restriction.

An alternative bariatric device 315 may further include a restriction component 33 restricting discharge of food from lumen 18 (FIG. 6). Restriction component 33 may be in the form of a chamber 34 extending within the lumen of body 316. In the illustrative embodiment, restriction component 33 is adjacent to distal portion 317c of wall 317, but could be at other locations along wall 317. Chamber 34 may be increased or decreased in volume utilizing various techniques, such as by adding or withdrawing a fluid, such as a gas or a liquid, via a blunt needle 26 (FIG. 7). Other known devices, such as an external electronic device that communicates with a control (not shown) and a pump/fluid reservoir within the patient, may be used to adjust the size of restriction component 33. With such configuration, the external control may actuate the pump through the internal control in order to increase or decrease the size of chamber 24. Alternatively, the internal control may be programmed to carry out the adjustment. Chamber 28 restricts the cross-section of lumen 18. Such restriction resists egress from lumen 18 of walls 16 and thereby resists the continued ingestion of food past device 315. This may be useful in patients who tend to continue to eat past satiety.

Figure 8:
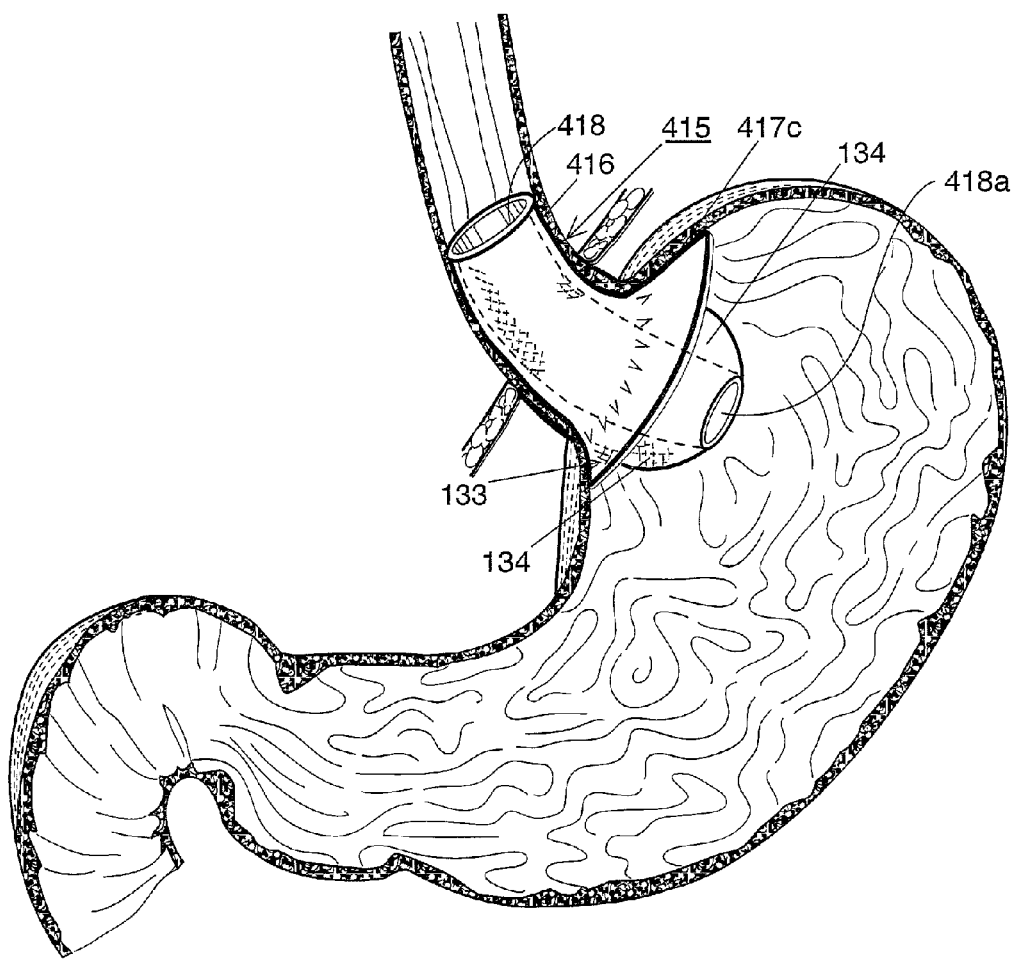
FIG. 8 is the same view as FIG. 2 of yet another alternative embodiment.

FIG. 8 illustrates an alternative bariatric device 415 having a body 416 with a restriction component 133 in the form of an inflatable reservoir or chamber 134 which surrounds the distal portion 418a of the lumen 418. Reservoir 134 provides an adjustable restriction wherein, as additional fluid is added to chamber 134, the increase in the volume of the chamber restricts the diameter of lumen 418 thereby adjusting the ability to resist egress from the lumen of bariatric device 415 thereby providing a variable restriction to ingestion of food. Chamber 134 may also be capable of increasing the external diameter of the device wall 417c thereby placing additional pressure on stretch receptors at the cardia of the patient's stomach.

Figure 9:
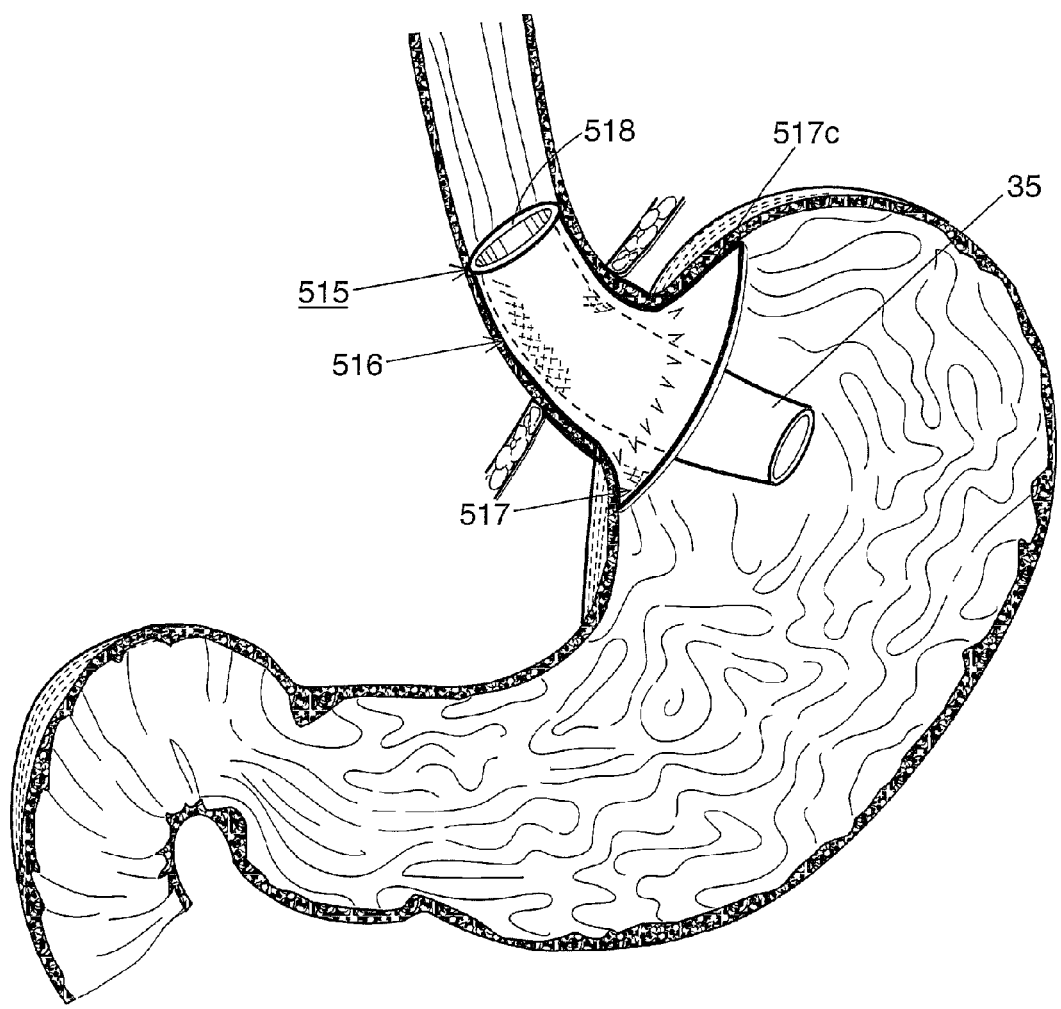
FIG. 9 is the same view as FIG. 2 of yet another alternative embodiment.

An alternative bariatric device 515 may include a body 516 having a wall 517 including an anti-reflux component 35 (FIG. 9). Anti-reflux component 35 may be in the form of a one-way valve in order to resist reflux from the stomach to the esophagus. As best seen in FIG. 9, anti-reflux component 35 may be in the form of a tubular extension of lumen 518 that expands to allow distal movement of food but collapses to reduce reflux.

Figure 10:
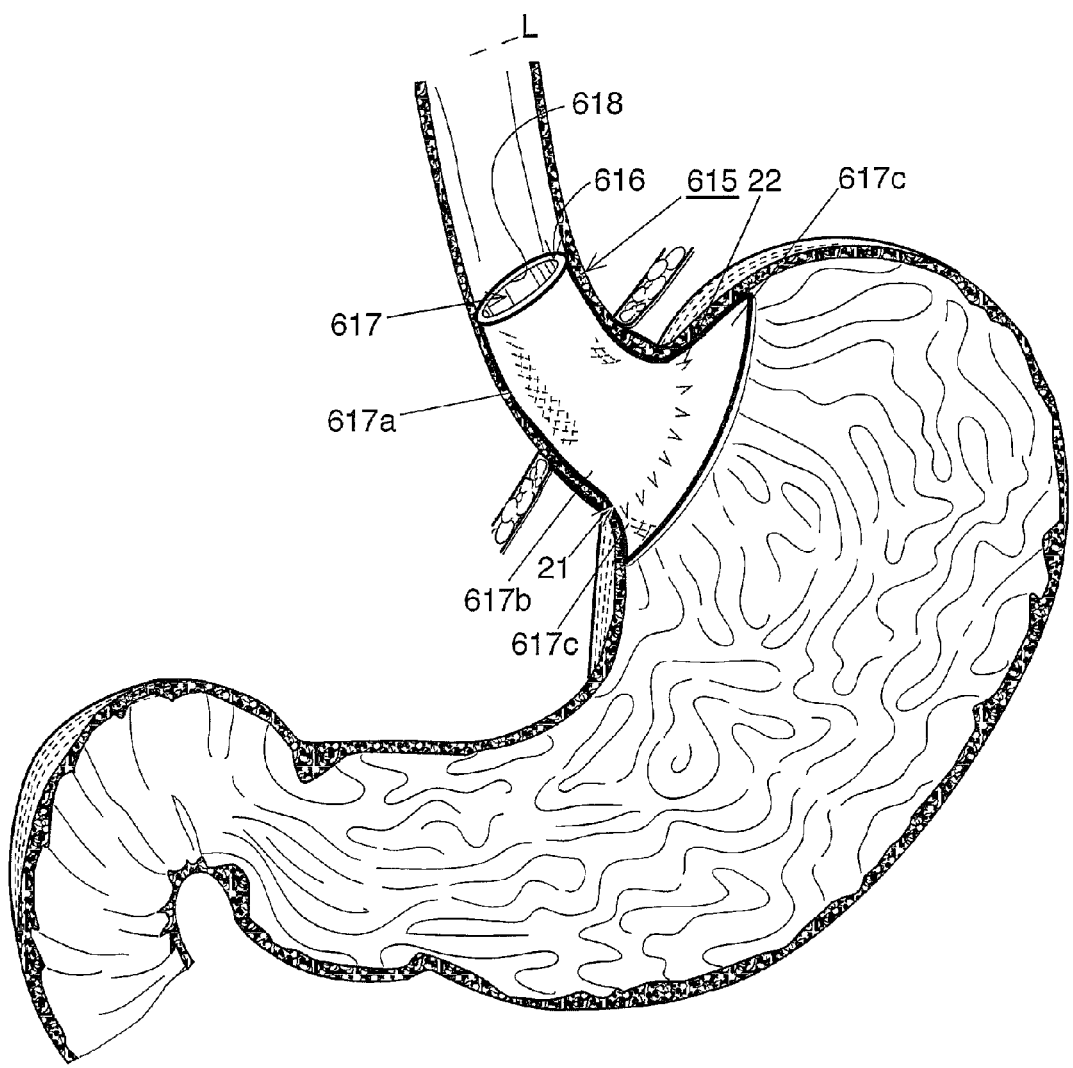
FIG. 10 is the same view as FIG. 1 of yet another alternative embodiment.

An alternative bariatric device 615 includes a body 616 having a wall 617 that is self-expandable at a proximal portion 617a, a middle portion 617b and a distal portion 617c, the latter being configured to the cardiac notch of the patient (FIG. 10). Bariatric device 615 includes a fixation system 21, such as a series of anchors 22, at the esophageal-gastric junction of the patient. The entire surface of wall 617 is made of a self-expanding material.

Figure 11:
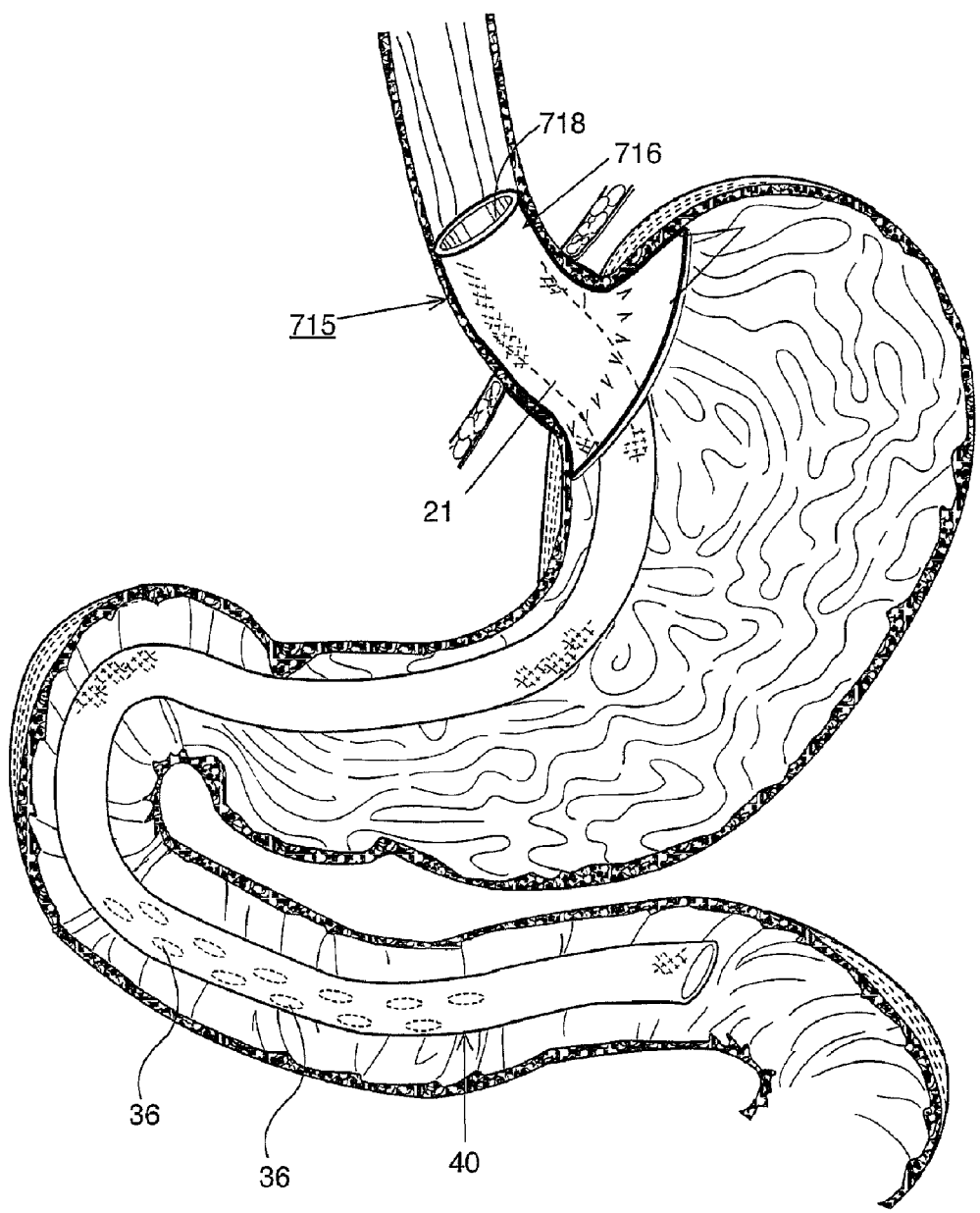
FIG. 11 is the same view as FIG. 1 of yet another alternative embodiment.

An alternative bariatric device 715 illustrated in FIG. 11 has a body 716 in which egress from the lumen 718 is from a discharge portion 40 of the device located at or near the patient's intestines. This provides additional weight loss by substantially bypassing the patient's stomach and discharging to the intestines. Device 715 may include a series of perforations 36 at discharge portion 40 in order to distribute the egress from lumen 718 along the small intestine of the patient. Use of bariatric device 715 may require dietary restrictions to avoid food collection in the elongated lumen.

Figure 12:
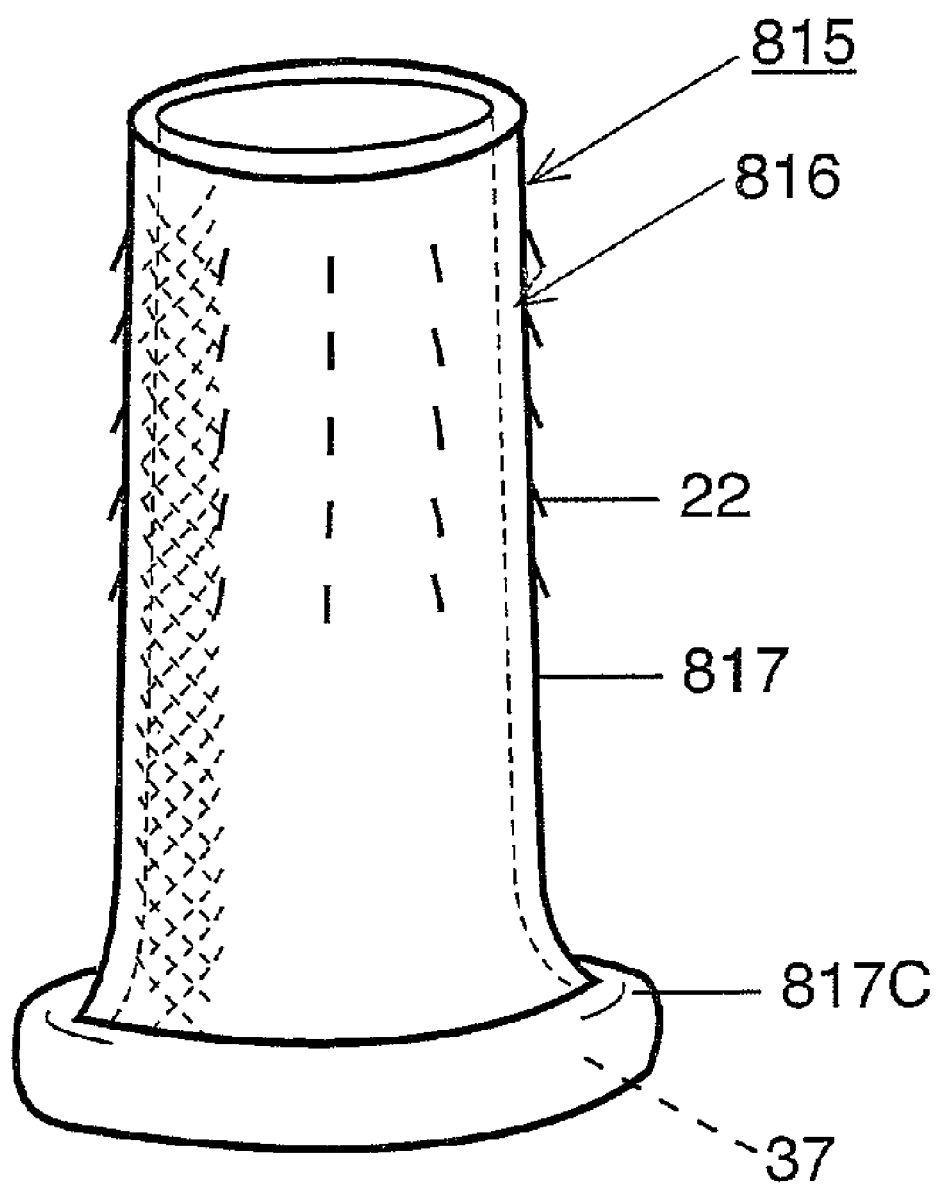
FIG. 12 is the same view as FIG. 2 of yet another alternative embodiment.
Figure 13:
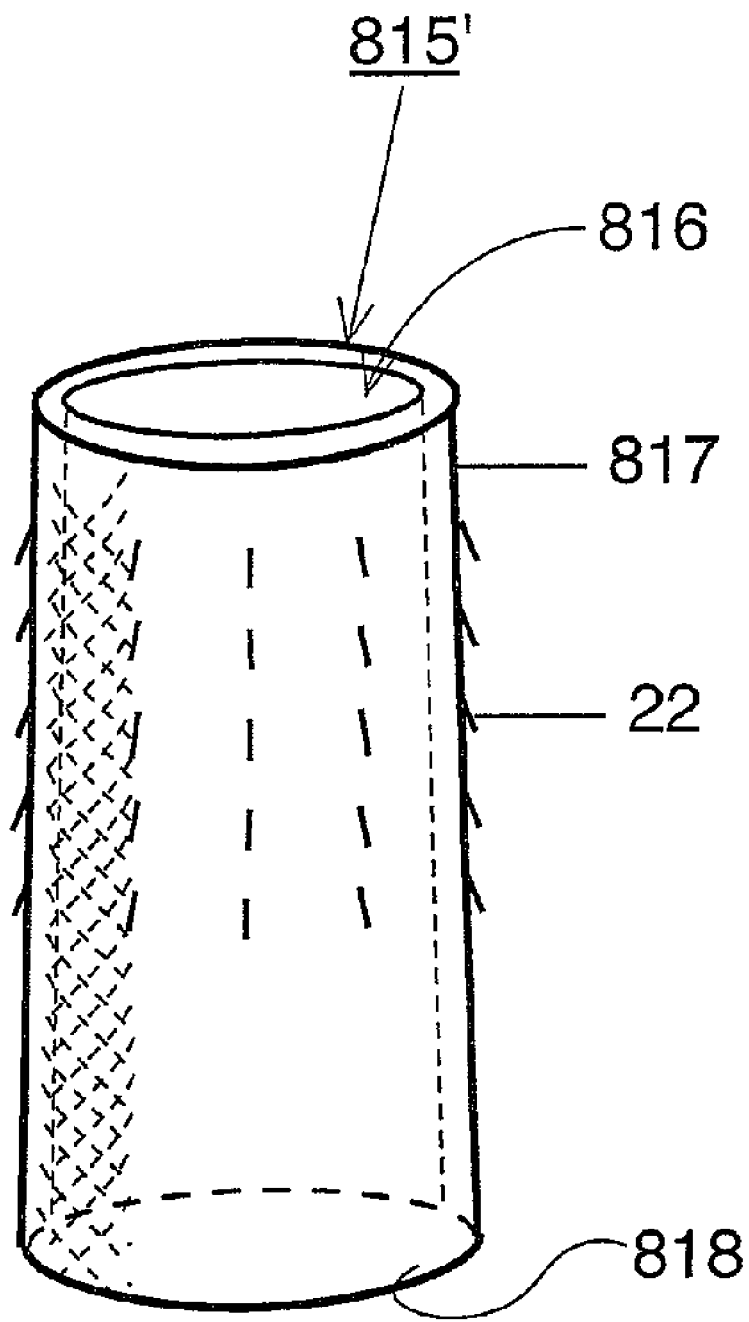
FIG. 13 is the same view as FIG. 2 of yet another alternative embodiment.

Anchors may be positioned at various locations along the exterior of the wall of the device. For an example, an alternative bariatric device 815 is illustrated in FIG. 12 with a body 816 having a wall 817 having anchors, such as V-shaped appendages, barbs, or hooks distributed along the outer wall of the body. The fixation system may also be in the form of a balloon-expandable wall 817c defining a chamber 37 that applies sufficient pressure on the conduit in which the device is located in order to resist distal migration of the device. The balloon can extend the device wall to produce fixation and can be deflated in order to allow the device to be removed. FIG. 13 illustrates an alternative bariatric device 815' having a body 816 with a wall 817 defining a lumen 818 without a chamber. Other fixation systems may be apparent to the skilled artisan, such as stitching, stapling, and the like.

Figure 14:
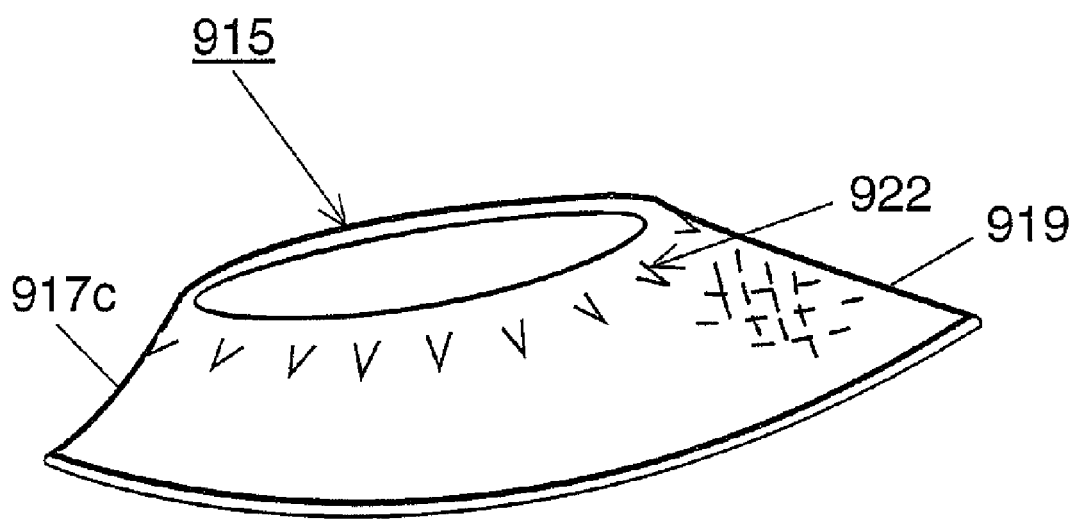
FIG. 14 is the same view as FIG. 2 of yet another alternative embodiment.

An alternative bariatric device 915 illustrated in FIG. 14 includes a body 916 having a wall 917 that is positioned virtually entirely within the patient's stomach. Wall 917 is of a size and shape to conform to the cardiac portion of the stomach, cardia, and is configured to exert pressure, typically radial pressure, on the cardia. Device 915 includes a fixation system 922 that engages the cardia or the esophageal-gastric junction.

Figure 14A:
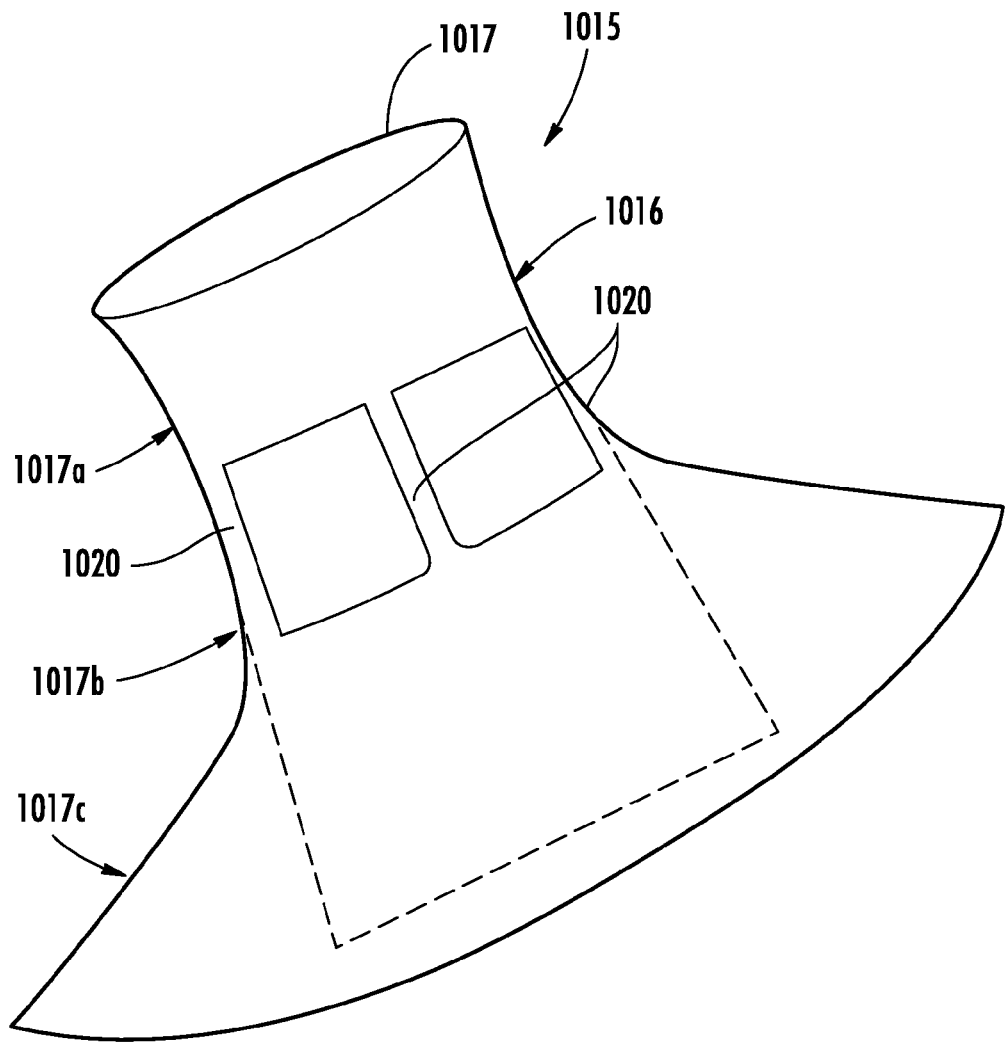
FIG. 14A is a perspective view of an alternate embodiment of the bariatric device of FIG. 1.

As noted above, the non-self-expanding portion of bariatric device of the present invention may be formed from discrete wall portions. Referring to FIG. 14A, device 1015 is of similar construction to device 15 and includes a body 1016 having an expandable wall 1017, which defines a lumen 1018. Wall 1017 is similar to wall 17 and includes a proximal portion 1017a to exert pressure on the abdominal portion of the esophagus and a distal portion 1017c that is configured to exert pressure on the cardia. For further details of portions 1017a and 1017c reference is made to the previous embodiments.

In the illustrated embodiment, the central portion 1017b of the body 1016 is formed from discrete wall portions 1020, which connect the proximal and distal portions 1017a, 1017c of wall 1017 together. Wall portions 1020 may act as tension members between the distal portion and the proximal portion and may further act as compression members to maintain the distal and proximal portions at a desired spacing, but which do not exert any significant outward or radial pressure on the gastro-esophageal junction. Wall portions 1020 may be generally equal in size and evenly spaced around the perimeter of body 1016 or may be unevenly spaced and, further, may have different widths and lengths. For example, the lengths of the wall portions may fall in a range of 0.75 cm to 1.5 cm. The number of wall portions may vary, with the illustrated embodiment depicting four wall portions that are generally evenly spaced around the perimeter of body 1016.

As noted above, wall portions 1020 optionally form a non-self-expanding portion of wall 1017 and align with the gastro-esophageal junction to allow the junction to function normally. The spaces between the wall portions 1020 may comprise holes or openings or may be filled by a flexible membrane or flaccid material.

In addition, wall portions 1020 may provide fixation points, for example, for sutures to secure device 1015 at or near the gastro-esophageal junction in which case the material forming wall portions 1020 may formed from a relatively stiff material, such as fibers or fibrous material, for example, embedded in silicone, for example.

Further, the upper open end or entrance of body 1016 may be flared outwardly to bear or seal against the esophageal wall to essentially close off the space or gap between device 1015 and the esophagus.

Various delivery systems may be utilized to deliver any of the bariatric devices 15-1015 to the patient. Such a delivery system may include a tube device (not shown) into which the bariatric device is compressed. The tube device may be a stiff or flexible tube and be sized and shaped to easily fit within the patient's esophagus. Such a delivery system includes a deployment mechanism (not shown) to retract the bariatric device from the tube. As the bariatric device is removed from the tube, it assumes its expanded form. If a self-expanding wall is utilized, the bariatric device will assert pressure, such as a generally radial pressure, on the distal esophagus and/or the cardia of the patient when removed from the tube. If an expandable wall is utilized, such as a bladder, the bladder is inflated in order to exert pressure. Various markers, such as fluorescent markers, may be applied to the wall of the bariatric device in order to allow for fluoroscopic assist in the placement of the device.

Figure 15:
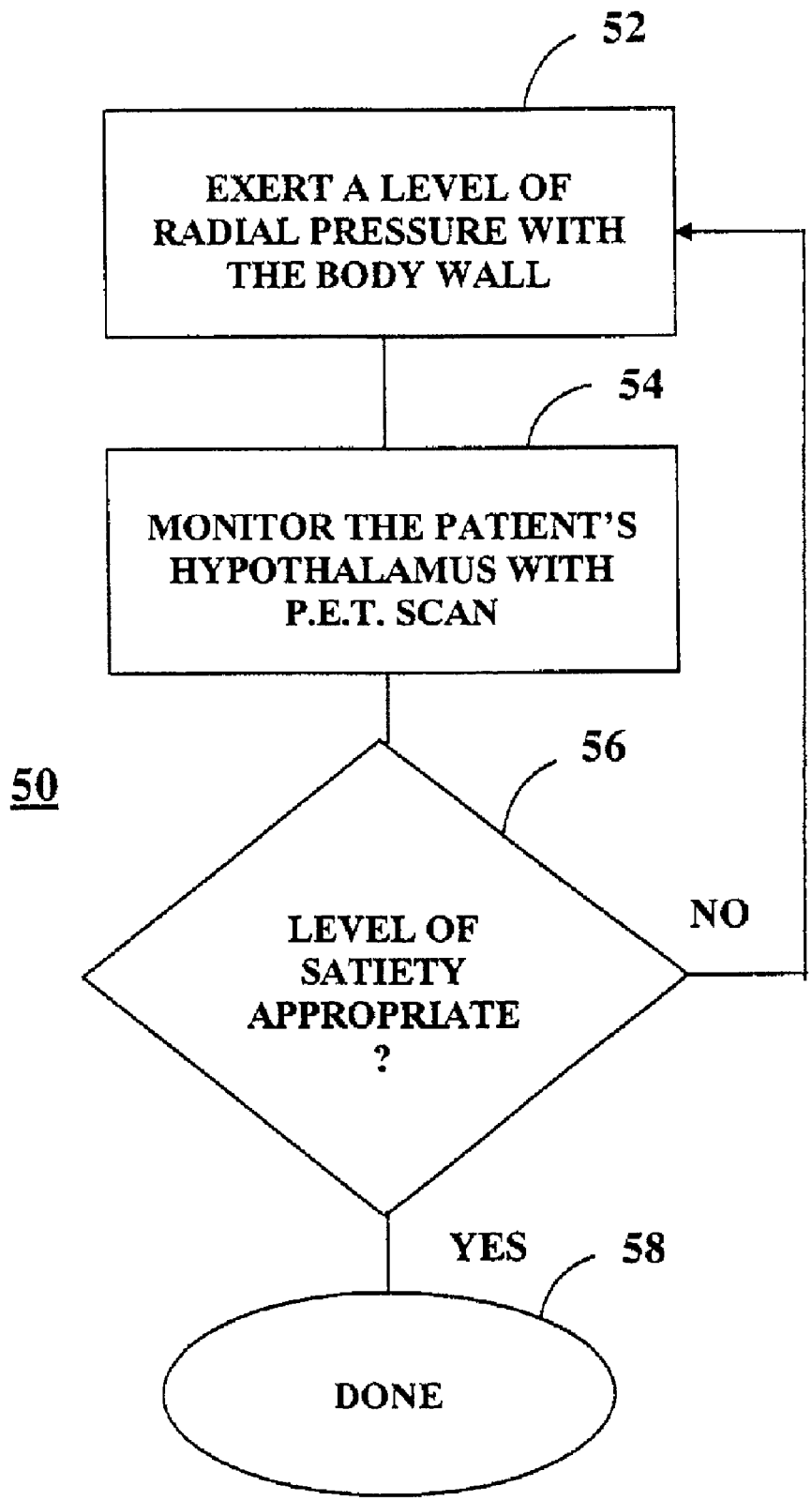
FIG. 15 is a block diagram of a technique for selecting the level of pressure exerted by the body wall.

A method 50 may be provided for monitoring and, if desired, adjusting the amount of satiety produced by the bariatric device and method (FIG. 15). In method 50, a bariatric device 15-1015 is inserted in the patient at 52 and a level of pressure, such as generally radial pressure, is applied by the body wall of the device. The level of satiety is monitored, such as by monitoring the patient's hypothalamus at 54, such as with a Positron Emission Tomography (P.E.T.) scan. The P.E.T. scan produces a visual image of the hypothalamus that changes colors with the amount of activity of the hypothalamus. By observing the color of the hypothalamus through the P.E.T. scan, a determination is made at 56 whether an appropriate level of satiety is obtained. If it is, then the procedure is done at 58.

If it is determined at 56 that an appropriate level of satiety is not being obtained, the process returns to 52 where a different level of pressure may be adjusted by the body. The adjustment of pressure may be in the form of adding or subtracting fluid from a bariatric device having an expandable wall by the use of a chamber 24. Alternatively, the adjustment of the pressure may be in the form of deploying a different size or characteristic device which is self-expandable and applies a different force to the patient through the self-expandable wall. The amount of satiety may be different for different patients. For example, a patient who is overweight may require a particular level of pressure, whereas a more obese, such as a morbidly obese, patient may require a higher level of satiety. Likewise, a child or an adolescent may require different levels of pressure. The ability to obtain immediate feedback on satiety strength allows the efficacy of the system to be established at deployment rather than monitoring the patient for weight loss and adjusting it after the patient has lost either too much or too little weight.

Alternately, the amount of satiety can be gauged by where the patient falls on the satiety continuum—that is whether they are hungry, satisfied, full or even nauseous. For a morbidly obese person, it may be desirable to apply sufficient pressure so that the patient is nauseous and then optionally reduced slightly so that the patient just below being nauseated or at a sub-nauseous level. This may be particularly useful when a remote control is being used in combination with an adjustable device where the patient may themselves adjust the level of pressure to maintain their desired or a prescribed level of satiety.

Any of the bariatric devices 15-1015 may be used as part of a multi-disciplinary comprehensive program. This may include the adjustment of medications as the patient experiences weight loss. For example, for patients taking diabetic medications, less insulin may be required as a patient loses weight. Also, blood pressure medications and other medications may be adjusted as the patient loses weight.

Because of the ability of the bariatric device 15-1015 to cause satiety, it is possible, in certain patients, that the patient will require nutritional supplements, such as protein liquids, in order to ensure adequate nutritional needs, such as protein intake. Also, anti-nausea medications may be given to the patient, especially at the beginning of the placement. This is because a bariatric device, according to the invention, may cause nausea at the beginning of the placement.

In order to reduce the likelihood of food getting caught in the lumen and in order to minimize interference with natural peristalsis in the esophagus, the length of the lumen is generally kept below 9 cm. In most embodiments, the length of the lumen is in the range of approximately 6 cm to approximately 7 cm. Widened portions of the body, such as distal portions 17c-1017c, are not considered part of the lumen for determining the length of the lumen. The expandable wall, whether self-expanding or balloon-expandable, should provide consistent pressure over as large an area as possible in order to induce adequate satiety, consistent with an effort to keep the lumen as short as possible.

Thus, it is seen that the present invention introduces a new category of weight loss techniques: implied satiation. The invention advantageously utilizes stretch receptors, such as those located at the abdominal portion of the esophagus and/or esophageal-gastric junction and/or the cardiac portion of the stomach of the patient to cause satiety. In contrast to gastric bypass surgery and adjustable gastric bands, the present invention does not require surgical intervention. In that regard, the present invention provides a non-invasive or minimally invasive alternative. However, the invention may be utilized in combination with known restrictive and/or malabsorptive techniques, such as gastric bypass surgery and adjustable gastric bands to further help the patient lose weight. Advantageously, the present invention may be applied to patients who are contraindicated for surgery, such as those with mildly high obesity and for those at risk for surgery. Also, the invention may be used to achieve sufficient weight loss in morbidly obese patients to stabilize the patient for gastric bypass surgery. Moreover, the present invention may be properly sized for use with children and adolescence. Thus, the present invention provides a non-intrusive or minimally intrusive technique for addressing the increasing epidemic of obesity in adolescents and children, as well as adults.

The present invention also comprehends an implied satietor that is capable of exerting pressure at the patient's abdominal portion of the esophagus, esophageal-gastric junction and/or cardia, such as by suitable dimensioning of a self-expanding wall or by a mechanism for expanding the wall outwardly. Examples of such a mechanism may be a bladder mechanism whereby the wall could exert varying pressures. The present invention also has the capability of assisting in reducing esophageal leakage. This may further enhance the use of the invention in combination with other techniques, such as gastric bypass surgery, esophageal tumors, and the like. In addition to influencing the neurohormonal feedback mechanism present at the abdominal portion of the esophagus, the present invention is capable of resisting egress from the lumen of the satiety device. This provides additional benefit to certain patients by resisting their ability to ingest food beyond satiety. Because the device may be inserted endoscopically with fluoroscopic assist, the device may be suitably and accurately positioned at the desired location within the patient's esophagus, esophageal-gastric junction and/or cardia and adjustments made to the satiety device as required. Moreover, the device may be subsequently removed from the patient if indicated. The use of various fixation systems allow the device to be positioned at or near the abdominal portion of the esophagus, the esophageal-gastric junction and/or the cardia while resisting distal migration of the device. Moreover, the use of such fixation system may allow for the satiety device to be readily removed from the patient.

Evidence of the viability of the invention can be seen by its principle having been reduced to practice and found to cause weight loss in patients. The patients, who ranged from non-obese to morbidly obese, lost weight, generally over a one or two week period during which the device was in place. The patients experienced some initial nausea. They reported satiety throughout placement of the device. When the device was no longer present, the patients regained hunger.

Changes and modifications in the specifically described embodiments can be carried out without departing from the principles of the invention which is intended to be limited only by the scope of the appended claims, as interpreted according to the principles of patent law including the doctrine of equivalents.

The embodiments of the invention in which an exclusive property or privilege is claimed are defined as follows:

1. A bariatric device comprising:
  a body having a wall defining a lumen, said wall configured to generally conform to the shape and size of at least one chosen from i) the abdominal portion of the esophagus and ii) the proximal cardiac portion of the stomach, said wall adapted to exert a force on the at least one chosen from i) the abdominal portion of the esophagus and ii) the proximal cardiac portion of the stomach thereby influencing a neurohormonal feedback mechanism to cause at least partial satiety by augmenting fullness caused by food and simulating fullness in the absence of food, wherein said body is adapted to adjust the force exerted by said wall.

2. The bariatric device as claimed in claim 1, wherein said force is adjustable endoscopically.

3. The bariatric device as claimed in claim 1, wherein said wall defines a chamber wherein adjustment of an amount of fluid in said chamber adjusts the force exerted by said wall.

4. The bariatric device as claimed in claim 3 including a port providing external access to said chamber.

5. The bariatric device as claimed in claim 1 including a control, said control is adapted to adjust the force exerted by said wall.

6. The bariatric device as claimed in claim 5, wherein said control is adapted to temporally adjust the force exerted by said wall.

7. The bariatric device as claimed in claim 6, wherein said control is programmed to adjust the force exerted by said wall based upon the time of day.

8. The bariatric device as claimed in claim 7, wherein said control is programmed to increase the force exerted by said wall during anticipated waking hours and to decrease the force exerted by said wall during anticipated sleeping hours.

9. The bariatric device as claimed in claim 7, wherein said control is programmed to increase the force exerted by said wall at anticipated eating times.

10. The bariatric device as claimed in claim 6, wherein said control is adapted to adjust the force exerted by said wall based upon hormonal levels.

11. The bariatric device as claimed in claim 5 including another control that is an external control and a radio-frequency link between said control and said external control.

12. The bariatric device as claimed in claim 1, wherein said body includes tissue in-growth characteristics.

13. The bariatric device as claimed in claim 1 wherein said body is made at least in part from an absorbable material.

14. The bariatric device as claimed in claim 1, wherein said lumen is substantially free of restriction.

15. The bariatric device as claimed in claim 1, wherein said wall is adapted to exert a force without the presence of food.

16. A bariatric device comprising:
  a body having a wall defining a lumen, wherein said wall includes a wall portion defining an esophageal member sized to conform to an abdominal portion of the esophagus, another wall portion defining a cardiac member sized to conform to a proximal cardiac portion of the stomach and a further wall portion extending between said esophageal member and said cardiac member, wherein said esophageal member and said cardiac member are adapted to exert a force on the abdominal portion of the esophagus and the proximal cardiac portion of the stomach thereby influencing a neurohormonal feedback mechanism to cause at least partial satiety by augmenting fullness caused by food and simulating fullness in the absence of food, wherein said body is adapted to adjust the force exerted by said esophageal member and said cardiac member.

17. A bariatric device comprising:
  a body having a wall defining a lumen, said wall configured to generally conform to the shape and size of at least one chosen from i) the abdominal portion of the esophagus and ii) the proximal cardiac portion of the stomach, said wall adapted to exert a force on the at least one chosen from i) the abdominal portion of the esophagus and ii) the proximal cardiac portion of the stomach thereby influencing a neurohormonal feedback mechanism to cause at least partial satiety by augmenting fullness caused by food and simulating fullness in the absence of food; and
  a mechanism incorporated into said body, said mechanism being adapted to increase or decrease the force exerted on the at least one chosen from i) the abdominal portion of the esophagus and ii) the proximal cardiac portion of the stomach.

18. A method of causing at least partial satiety comprising:
  positioning a body at at least one chosen from i) an abdominal portion of the esophagus and ii) a proximal cardiac portion of the stomach, said body having a wall defining a lumen, said wall configured to generally conform to the shape and size of the at least one chosen from i) the abdominal portion of the esophagus and ii) the proximal cardiac portion of the stomach;
  exerting force with the wall at the at least one chosen from i) the abdominal portion of the esophagus and (ii) the proximal cardiac portion of the stomach thereby influencing a neurohormonal feedback mechanism of the patient to cause at least partial satiety by augmenting fullness caused by food and simulating fullness in the absence of food; and adjusting the force exerted with said wall.

19. The method as claimed in claim 18 wherein said adjusting includes increasing or decreasing the force exerted with said wall.

20. The method as claimed in claim 19 including monitoring a level of satiety.

21. The method as claimed in claim 18 including monitoring a level of satiety.

22. The method as claimed in claim 18 wherein said adjusting the force includes adjusting the force at the time of positioning said body.

23. The method as claimed in claim 18 wherein said adjusting the force comprises adjusting the force according to a temporal parameter.

24. A method of causing at least partial satiety comprising:
positioning a body at the abdominal portion of the esophagus and the proximal cardiac portion of the stomach, said body having a wall defining a lumen, wherein said wall includes a wall portion defining an esophageal member sized to conform to the abdominal portion of the esophagus, another wall portion defining a cardiac member sized to conform to the proximal cardiac portion of the stomach and a further wall portion extending between said esophageal member and said cardiac member;

exerting a force with said esophageal member and said cardiac member on the abdominal portion of the esophagus and the proximal cardiac portion of the stomach thereby influencing a neurohormonal feedback mechanism to cause at least partial satiety by augmenting fullness caused by food and simulating fullness in the absence of food; and increasing or decreasing said force exerted with said esophageal member and said cardiac member.

25. A method of causing at least partial satiety comprising:
positioning a body at at least one chosen from i) an abdominal portion of the esophagus and ii) a proximal cardiac portion of the stomach, said body having a wall defining a lumen, said wall configured to generally conform to the shape and size of the at least one chosen from i) the abdominal portion of the esophagus and ii) the proximal cardiac portion of the stomach;

exerting force with the wall at the at least one chosen from i) the abdominal portion of the esophagus and (ii) the proximal cardiac portion of the stomach thereby influencing a neurohormonal feedback mechanism of the patient to cause at least partial satiety by augmenting fullness caused by food and simulating fullness in the absence of food; and wherein said body further comprises a mechanism that is adapted to adjust the force exerted on the at least one chosen from i) the abdominal portion of the esophagus and ii) the proximal cardiac portion of the stomach; and increasing or decreasing said force using said mechanism.

* * * * *